(12) United States Patent
Dasgupta et al.

(10) Patent No.: US 9,459,210 B2
(45) Date of Patent: Oct. 4, 2016

(54) STATIC MAGNETIC FIELD INDUCED DIFFERENTIAL FLUORESCENCE EMISSION

(75) Inventors: Anjan Kr. Dasgupta, Kolkata (IN); Sufi Oasim Raja, Kolkata (IN)

(73) Assignee: UNIVERSITY OF CALCUTTA, Kolkata (IN)

( * ) Notice: Subject to any disclaimer, the term of this patent is extended or adjusted under 35 U.S.C. 154(b) by 717 days.

(21) Appl. No.: 13/884,721

(22) PCT Filed: Aug. 6, 2012

(86) PCT No.: PCT/IB2012/001501
§ 371 (c)(1),
(2), (4) Date: May 10, 2013

(87) PCT Pub. No.: WO2013/167933
PCT Pub. Date: Nov. 14, 2013

(65) Prior Publication Data
US 2013/0300865 A1    Nov. 14, 2013

(30) Foreign Application Priority Data
May 8, 2012 (IN) .............. 512/KOL/2012

(51) Int. Cl.
*G01N 21/64* (2006.01)
*G01N 33/68* (2006.01)
*G01N 33/48* (2006.01)

(52) U.S. Cl.
CPC .......... *G01N 21/64* (2013.01); *G01N 21/6408* (2013.01); *G01N 21/6428* (2013.01); *G01N 21/6486* (2013.01); *G01N 33/48* (2013.01); *G01N 33/68* (2013.01)

(58) Field of Classification Search
CPC ............. G01N 21/64; G01N 21/6408; G01N 21/6428; G01N 21/6456; G01N 21/6486; G01N 33/48; G01N 33/68
USPC ...... 436/63, 86, 149, 150, 164, 172; 435/29, 435/366, 288.7; 422/82.05, 82.08; 250/459.1, 461.2, 462.1; 356/417
See application file for complete search history.

(56) References Cited

U.S. PATENT DOCUMENTS 3,656,835 A * 4/1972 Johnson .................... G02F 1/09
359/284
4,692,661 A 9/1987 Moskowitz et al.
(Continued)

OTHER PUBLICATIONS

Makarov et al. Journal of Chemical Physics, vol. 118, No. 1, Jan. 1, 2003, pp. 87-92.*
(Continued)

*Primary Examiner* — Maureen Wallenhorst
(74) *Attorney, Agent, or Firm* — Foley & Lardner LLP (57) ABSTRACT

Exposure to a static magnetic field changes the fluorescence intensity of a wide range of fluorophores, including small molecules (e.g., tryptophan), complex organizations of fluorophores (e.g., proteins), quantum dots, nanoparticles, and other materials. Different materials may experience different changes in fluorescence emission upon exposure to a magnetic field—for instance, some or all of a material's fluorescence emission spectrum may increase in amplitude or shift in wavelength. Different materials may also experience different changes in relaxation time, which is the time constant associated with fluorescence decay. These magnetically induced differences fluorescence emission spectra and decay can be used to identify, classify, or sort materials noninvasively.

19 Claims, 9 Drawing Sheets

(56) References Cited

U.S. PATENT DOCUMENTS

| | | | |
|---|---|---|---|
| 5,189,257 | A | 2/1993 | Borgmeyer et al. |
| 5,485,530 | A | 1/1996 | Lakowicz et al. |
| 5,789,257 | A | 8/1998 | Tapper et al. |
| 6,031,373 | A | 2/2000 | Szeles et al. |
| 7,106,051 | B2 | 9/2006 | Prins et al. |
| 2003/0143429 | A1 | 7/2003 | Suzuki et al. |
| 2005/0069497 | A1* | 3/2005 | Long ............... A61B 5/0059 424/9.2 |
| 2006/0256338 | A1 | 11/2006 | Gratton et al. |
| 2007/0166730 | A1 | 7/2007 | Menon et al. |
| 2009/0321662 | A1 | 12/2009 | Ohtsuka |
| 2010/0248257 | A1* | 9/2010 | Jacobsen ........... A61K 47/4823 435/7.1 |
| 2010/0329933 | A1 | 12/2010 | Schulz et al. |
| 2011/0044527 | A1 | 2/2011 | Tibbe et al. |
| 2011/0168918 | A1 | 7/2011 | Wimberger-Friedl et al. |

OTHER PUBLICATIONS

Raja, S.O., and Dasgupta, A.K., "Magnetic Field Induced Self Assembly and Optical memory of pi-Ring containing Fluorophores," Chemical Physics Letters, 3, pp. 19 (Dec. 2012).

ASGE Technology Committee, "Autofluorescence imaging," Gastrointestinal Endoscopy, vol. 73, No. 4, pp. 647-650 (2011).

Ball, P., "The dawn of quantum biology" Nature, vol. 474 (2011).

Cai, J. Guerreschi, G. G. Briegel, H. J., "Quantum Control and Entanglement in a Chemical Compass", Phys. Rev. Lett.104 (2010).

Chakraborty, B. Basu, S., "Interaction of proflavin with aromatic amines in homogeneous and micellar media: Photoinduced electron transfer probed by magnetic field effect", Chemical Physics Letters 487 (2010) 51-57.

Chen, et al., "Graphene Oxide Based Photoinduced Charge Transfer Label-Free Near-Infrared Fluorescent Biosensor for Dopamine", Anal. Chem., 2011, 83 (22), pp. 8787-8793 DOI: 10.1021/ac2023537.

Colvin, M. T. et al., "Magnetic Field-Induced Switching of the Radical-Pair Intersystem Crossing Mechanism in a Donor-Bridge-Acceptor Molecule for Artificial Photosynthesis" J. Am. Chem. Soc. 133, 5 (2011).

E. Reyes et al., "Enhancement of Confocal Fluorescence Images of Neutrophils by Magnetic Fields," Microscopy and Analysis, vol. 22, No. 3, pp. 21-22 (May 2008).

Gauger, E. M. Rieper, E. Morton, J. J. L. Benjamin, S. C. Vedral, V., "Sustained Quantum Coherence and Entanglement in the Avian Compass", Phys. Rev. Lett. 106 (2011).

Geacintov, N. Pope, M. and Vogel, F., "Effect of Magnetic Field on the Fluorescence of Tetracene Crystals: Exciton Fission" Phys. Rev. Lett. 22, 12 (1969).

Groff, R. P. Avakian, P. Merrifield, R., "Coexistence of Exciton Fission and Fusion in Tetracene Crystals", Phys. Rev. B. 1, 2 (1970).

Iida, A. Yamaguchi, S., "Intense solid-state blue emission with a small Stokes' shift: pie-stacking protection of the diphenylanthracene skeleton", Chem. Commun. 7345, 21 (2009).

International Search Report and Written Opinion in PCT/IB2012/001501 mailed Dec. 6, 2012.

N. Ohta, "Magnetic Field Effects on Fluorescence in Isolated Molecules with the Intermediate Level Structure of Singlet212Triplet Mixed States," J. Physical Chemistry, vol. 100, pp. 7298-7316 (1996), DOI: 10.1021/jp9517514.

Panitchayangkoon, G. et al., "Long-lived quantum coherence in photosynthetic complexes at physiolocial temperature", Proc. Natl. Acad. Sci. 107, 29 (2010).

Pérez-Prieto, J. Galian, R. E. Maria C. Morant-Miñana Miguel A. Miranda., "Steady-state and time-resolved studies on the formation of skatolyl radicals photosensitized by 2-benzoylthiophene", Photochem. Photobiol. Sci. 2 (2003).

Prezhdo, O.V., "Relationship between Quantum Decoherence Times and Solvation Dynamics in Condensed Phase Chemical Systems", Phys. Rev. Lett. 81, 21 (1998).

Ritz, T. et al., "Magnetic Compass of Birds is Based on a Molecule with Optimal Directional Sensitivity", Biophysical Journal 96, 8 (2009) 3451-3457.

Satoshi Moriyama, et al., "Fabrication of quantum-dot devices in graphene", Sci. Technol. Adv. Mater. 11 (2010) 054601 (5pp) doi:10.1088/1468-6996/11/5/054601.

Sonneveld, A. Duysens Louis, N. M. Moerdijk, A., "Magnetic field-induced increase in chlorophyll a delayed fluorescence of photosystem II: A 100- to 200-ns. component between 4.2 and 300K" Proc. Natl. Acad. Sci. 77, 10 (1980).

Umeki, T., et al. "Theory of macroscopic quantum coherence in d-wave superconductor junctions", Physica C: Superconductivity 463-465 (2007).

Voznyak et al., "Magnetic field-induced fluorescence changes in chlorophyll-proteins enriched with P-700", Biochim Biophys Acta, Sep. 5, 1980.

Wang, et al., "Graphene Oxide—Peptide Conjugate as an Intracellular Protease Sensor for Caspase-3 Activation Imaging in Live Cells"—Angewandte Chemie International Edition DOI: 10.1002/anie.201101351, 2011.

Yang et al., "Optical imaging through scattering media via magnetically modulated fluorescence", Optics Express, vol. 18, No. 25, Dec. 6, 2010.

* cited by examiner

STATIC MAGNETIC FIELD INDUCED DIFFERENTIAL FLUORESCENCE EMISSION

CROSS-REFERENCE TO RELATED APPLICATIONS

The present application is a U.S. national stage application under 35 U.S.C. §371 of International Application No. PCT/IB2012/001501, filed on Aug. 6, 2012, which claims the priority benefit of Indian Application No. 512/KOL/2012, filed on May 8, 2012. The entire contents of these applications are incorporated herein by reference in their respective entireties.

BACKGROUND

Nuclear magnetic resonance (NMR) has become an indispensible tool for chemists, biologists, and medical professionals. NMR is based on splitting of the spin energy states induced by a static magnetic field, and resonant absorption of electromagnetic energy, at levels equivalent to the energy difference between such split spin states. The resonance associated with energy absorption from the electromagnetic field occurs in the microwave region. Thus, NMR, unless aided by extensive modifications like stripe sensor tomography, is unsuitable for bio-imaging on the micron scale because the microwave fields required to produce resonant absorption have wavelengths on the order of millimeters. Other magnetic-resonance-based spectroscopy techniques, including electron spin resonance (ESR), also rely on excitation in the microwave region. While ESR can be successfully employed to study macroscopic parameters like membrane fluidity, the resolution of microwave radiation limits the usefulness of ESR in of bio-imaging.

SUMMARY

One embodiment of the present disclosure relates to a system and method of differentiating a fluorescent region in a sample, which may include a biological sample, a tissue, a cell, a protein, a quantum dot, bacterial chlorophyll, plant chlorophyll, or a particle tagged with a fluorophore. In one example, actuating a switch causes a magnet to apply a magnetic field to the fluorescent region. Inducing fluorescence of the fluorescent region with a light source or other radiation source; measuring a relaxation time associated with a decay of the fluorescence of the fluorescent region; and identifying at least part of the fluorescent region based on the relaxation time. For instance, the system may include a camera or other imaging device that acquires image data of the fluorescent region undergoing fluorescent decay and stores the data in a memory. A processor coupled to the memory may estimate or derive the relaxation time from the image data and identify or classify the fluorescent region based on the relaxation time.

In at least one example, applying the magnetic field includes setting the magnetic field's strength to a value from about 35 mT to about 100 mT. Applying the magnetic field may also include orienting the magnetic field vector parallel to the electric field vector associated with an electromagnetic field used to induce fluorescence of the fluorescent region, e.g., by rotating or translating the sample, the magnet, or the excitation source. The magnetic field vector can also be varied, e.g., to be perpendicular, anti-parallel, or at an angle with respect to the electric field vector. The processor may estimate or determine a change in the fluorescence as a function of the magnetic field vector's orientation and identify the fluorescent region based on the change in the fluorescence. The processor may also actuate a sorting device, such as a valve or ink-jet-style electrostatic deflector, to sort the fluorescent region or the sample based on the relaxation time.

Another embodiment of the present disclosure includes a system and associated method for discriminating a fluorescent region of a sample, such as a biological sample, a tissue, a cell, a particle, a protein, or a particle tagged with a fluorophore. A processor may determine a first relaxation time of the fluorescent region in the absence of a magnetic field (e.g., after withdrawal of a magnetic field) based on time-resolved image data (e.g., video imagery) or other suitable data. For instance, the first relaxation time may represent a photo-bleaching time, or relaxation caused by background cellular processes that are not affected by magnetic fields. The processor may also determine a second relaxation time of the fluorescent region in the presence of the magnetic field based on time-resolved image data (e.g., video imagery) or other suitable data. The processor may compare the first relaxation time to the second relaxation time and identify or classify the fluorescent region based on the comparison of the first relaxation time to the second relaxation time.

In one example, the system includes a magnet that can be used to generate and apply a magnetic field with a strength of about 35 mT to about 100 mT to the sample. The system may also include a camera or other imaging device that obtains a first series of images (time-resolved image data) of the fluorescent region under the magnetic field and a second series of images (time-resolved image data) of the fluorescent region in the absence of the magnetic field. The processor may determine a change in a first fluorescence spectrum associated with the fluorescent region from the first series of images and a change in a second fluorescence spectrum associated with the fluorescent region from the second series of images.

The processor may also compare the change in the first fluorescence spectrum to the change in the second fluorescence spectrum. Alternatively, or in addition, the processor may discriminate between one part of the fluorescent region and another part of the fluorescent region based on the comparison of the first relaxation time to the second relaxation time. The processor may also determine or estimate a change in an emission wavelength of the fluorescent region in the presence of the magnetic field.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The accompanying drawings, which are incorporated in and constitute a part of this specification, illustrate embodiments of the disclosed technology and together with the description serve to explain principles of the disclosed technology.

DETAILED DESCRIPTION

Exposing a sample to a static magnetic field before and/or during photo-excitation can enhance the intensity of the emitted fluorescent light. Without being limited to a particular theory, the mechanisms responsible for this fluorescence enhancement may include triplet state fusion to a higher singlet state (as observed in tetracene crystals) and Zeeman splitting in radical pair (RP) systems (like Chlorophyll-a solution). This magnetically induced enhancement occurs in quantum dots or proteins, and it may differ for different quantum dots or proteins. Since a protein is an ensemble of fluorescent amino acids, such as tryptophan and tyrosine, these amino acids may react differently to a magnetic field when free versus when part of a protein.

A fluorescent material may also retain this enhancement effect even after withdrawal of the magnetic field; as a result, the resulting relaxation behavior of the emitted fluorescent light may provide a signature of the fluorescent material. The time constant associated with the decay in fluorescence emission is called the relaxation time, $T_F$, and may be on the order of seconds. The relaxation time itself is different for different molecules, such as quantum dots, tryptophan, and different proteins, and can be measured at any temperature at which spectroscopic detection or imaging is permissible, e.g., room temperature. The spatial resolution associated with such an optical relaxation process may follow the optical resolution limit, which is much finer than the microwave resolution. These magnetically induced fluorescence enhancement patterns and fluorescence relaxation patterns can be used to identify or classify quantum dots, organic molecules, aromatic amino acids, proteins, and other fluorescent materials. Applications for the identification and classification techniques disclosed herein include, but are not limited to fluorescence spectroscopy, fluorescence microscopy, confocal microscopy, and flow cytometry.

In one example, this discrimination process involves applying a static magnetic field, at room temperature, to induce the enhancement of fluorescence or auto-fluorescence of some or all of a fluorescent material, such as tryptophan, tyrosine, proteins, quantum dots, nanoparticles, or other material. An imaging device, camera, or other detector collects data related to the relaxation time, which is on the order of seconds. A processor estimates or determines the relaxation time from the collected data and may generate a relaxation image (similar to a $T_1$ image or $T_2$ image in magnetic resonance imaging) at optical resolution (e.g., micron-scale resolution), which is much finer than the millimeter-scale resolution of radio-frequency imaging techniques.

Apparatus for Identifying or Classifying Fluorescent Samples

Figure 1A:
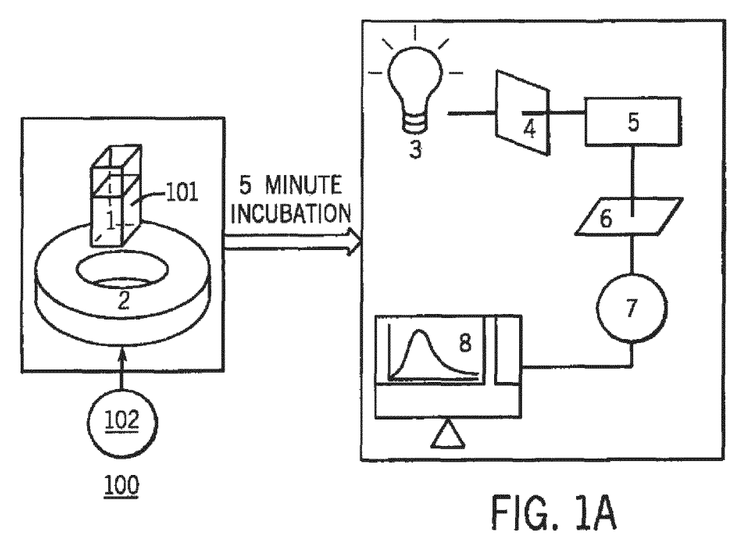
FIG. 1A illustrates a system configured to differentiate a fluorescent region in a sample by acquiring time-resolved imagery of the sample in the presence and absence of a magnetic field.

FIG. 1A illustrates an apparatus 100 suitable for identifying or classifying a region in a fluorescent sample based on the region's magnetically induced fluorescence pattern, its relaxation pattern, or both. The apparatus 100 includes a first sample holder 1 configured to hold a fluorescent sample 101 within a magnet 2, which may be a permanent magnet, electromagnet, thermally insulated electromagnet, or any other suitable magnetic field source, actuated by a switch 102. The magnet 2 may produce a magnetic field with a strength experienced by the sample 101 of about 0.005 Tesla, 0.010 Tesla, 0.025 Tesla, 0.035 Tesla, 0.050 Tesla, 0.00.10 Tesla, 0.075 Tesla, or any other suitable value. If the magnet 2 is or includes an electromagnet, its strength may be tuned between a range of values, e.g., between about 0.000 Tesla and about 0.100 Tesla. In some cases, the switch 102 simply turns the magnetic field on or off; in other cases, it controls the magnetic field's intensity, orientation, or both, e.g., by controlling a current or voltage applied to an electromagnetic or by controlling the magnet's position with respect to the sample 101.

The apparatus 100 also can include a light source 3, such as a 150 W helium lamp or laser, an (optional) excitation monochromator 4, such as a slit/grating combination or filter; a second sample holder 5; an emission monochromator 6, such as a slit/grating combination or filter; a detector 7, such as a photomultiplier tube, avalanche photodiode, or charge-coupled device (CCD); and a processor 8 with a display.

To use the apparatus 100, the user can place the fluorescent sample 101 in the first sample holder 1, then places the first sample holder 1 within the magnetic field generated by the magnet 2. The user leaves the sample 101 and the first sample holder 1 within the magnetic field for a suitable period of time (e.g., 30 s, 1 minutes, 2 minutes, 5 minutes, or 10 minutes), then moves the sample 101 from the first sample holder 1 to the second sample holder 5. Alternatively, the apparatus may include just one sample holder that holds the sample 101 such that the sample 101 experiences both the optical excitation from the light source 3 and the magnetic field from the magnet 2 (e.g., as described with respect to FIG. 1B).

Once the sample 101 is secured within the second sample holder 5, light from the light source 3 excites the sample 101, causing the sample 101 to fluoresce. Fluorescent light from the sample 101 propagates through the emission monochromator 6, which attenuates or reflects light at the excitation wavelength and transmits light at the emission wavelength. The fluorescent light transmitted through the emission monochromator 6 illuminates the detector 7, which produces an electrical signal, such as a photocurrent. whose amplitude varies with the intensity of the detected light. The processor 8 receives this electrical signal from the detector 7 and identifies or classifies at least part of the sample 101 based at least in part on the electrical signal, e.g., as described below.

Figure 1B:
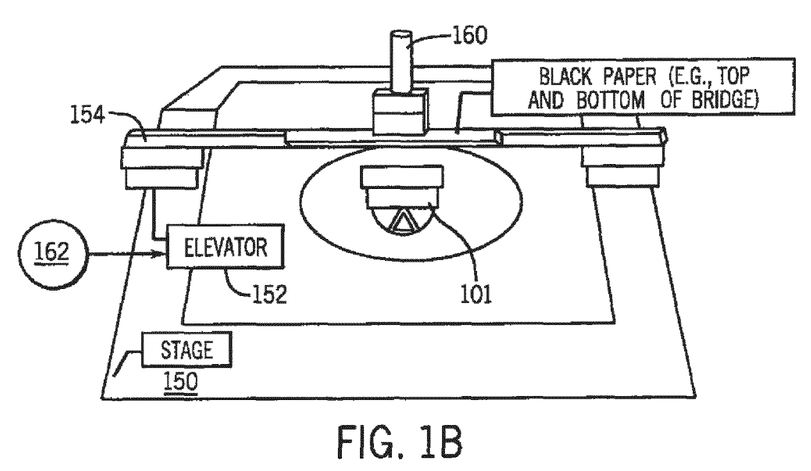
FIG. 1B illustrates an arrangement for acquiring time-resolved imagery of a sample in the presence and absence of a magnetic field.

FIG. 1B illustrates another arrangement suitable for identifying or classifying a region in a fluorescent sample based on the region's magnetically induced fluorescence pattern, its relaxation pattern, or both. A stage 150 holds the sample 101 in or near the image plane of a microscope objective or other lens (not shown) that forms part of a fluorescence microscope, confocal microscope, or any other suitable imaging system. As understood by those of skill in the art, the stage 150 can translate or rotate the sample 101 as desired (e.g., about or along each of two, three, four, five, or six different axes) with respect to the objective. The stage 150 also includes an elevator 152 and a plastic bridge 154 that support a magnet 160 that generates a magnetic field.

The magnet 160 may be a permanent magnet or a variable magnet, such as an electromagnet, whose strength can be modulated or varied as desired using a switch 162 that controls the elevator 152. The switch 162 may actuate the elevator 152 so as to push the magnet 160 closer to the sample 101 or further away from the sample 101. Alternatively, the switch 12 may turn a variable magnet on to a preset strength (e.g., 0.07 Tesla) for several minutes, then turn the magnet off. The switch 162 may also cause a variable magnet to pulse on and off repetitively or step through a series of increasing or decreasing field strengths. Removing the magnet 160 from the stage altogether also changes the field strength experienced by the sample 101.

In operation, a video camera, CCD array, or other imaging device (not shown) in optical communication with the sample 101 via the objective acquires images of at least a portion of the sample 101. The imaging device may acquire time-resolved imagery (e.g., video imagery) when the sample 101 is subject to the magnetic field 164 or when the sample 101 is not subject to the magnetic field. The imaging device may acquire this time-resolved imagery at a rate of dozens to thousands of frames per second (e.g., with 1 ms between successive frames) with a spatial resolution on the order of microns (e.g., about 0.5 µm or about 1.0 µm) using techniques known in the art. A memory (not shown) coupled to the imaging device may store this imagery for real-time processing or post-processing by a processor (e.g., processor 8 in FIG. 1A). In some cases, the memory may store a library or database representing the kinetics of fluorescence enhancement and relaxation for different fluorophores. The processor 8 may compare the acquired data to the data stored in the library or database to identify the sample 101.

Figure 1C:
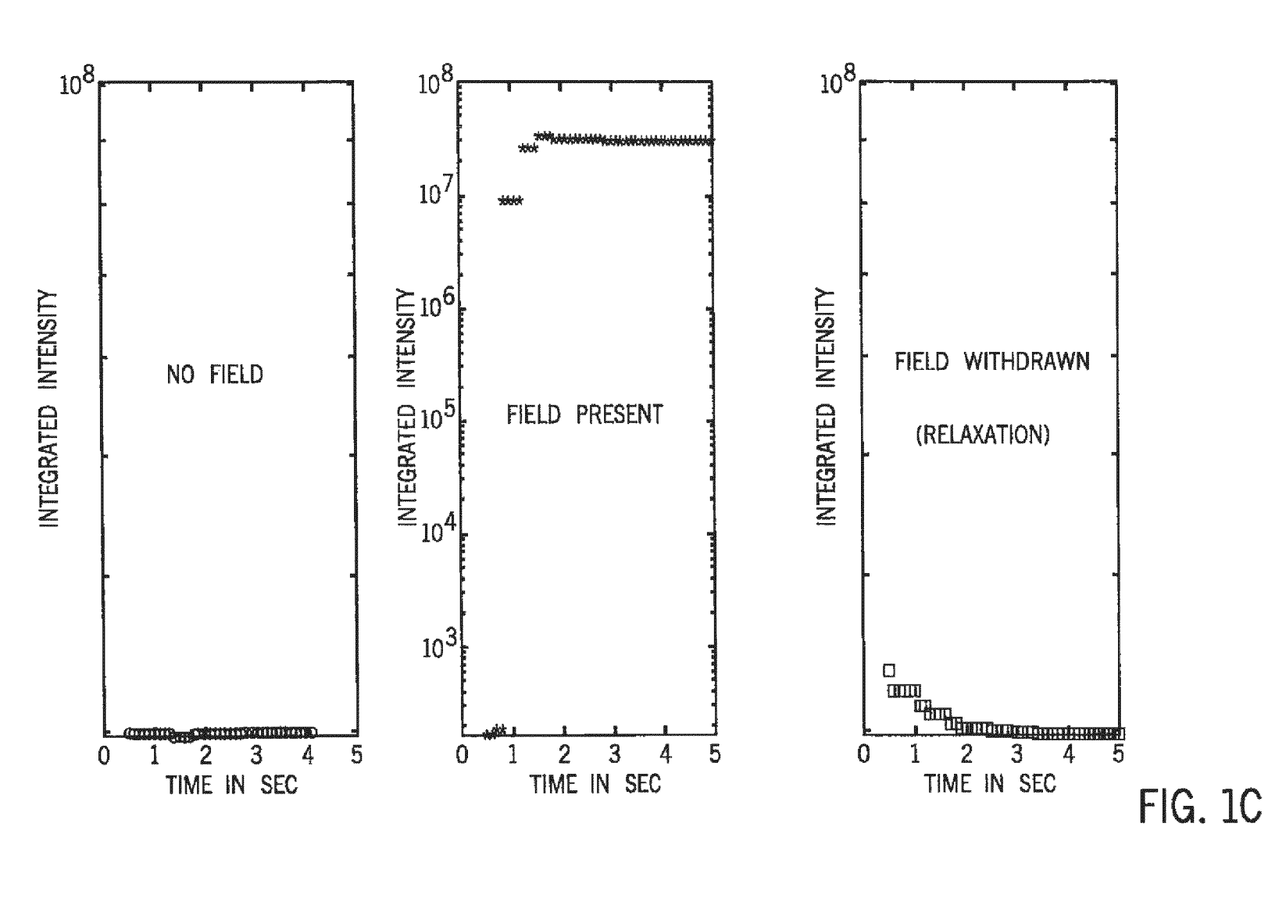
FIG. 1C shows the integrated intensity emitted by the sample over time with no magnetic field present (left plot), with a magnetic field present (middle plot), and shortly after withdrawal of the magnetic field (right plot).

FIG. 1C includes representative plots of fluorescence intensity versus time acquired using the arrangement of FIG. 1B for a sample with no magnetic field present (left plot), a magnetic field present (middle plot), and shortly after the magnetic field was removed (right plot). The y axis of each plot represents the intensity integrated over the entire image. The intensity is at a minimum value with no field present. Introducing the field causes the intensity to jump significantly, and removing the field causes the intensity to decay back to the minimum value.

Figure 1D:
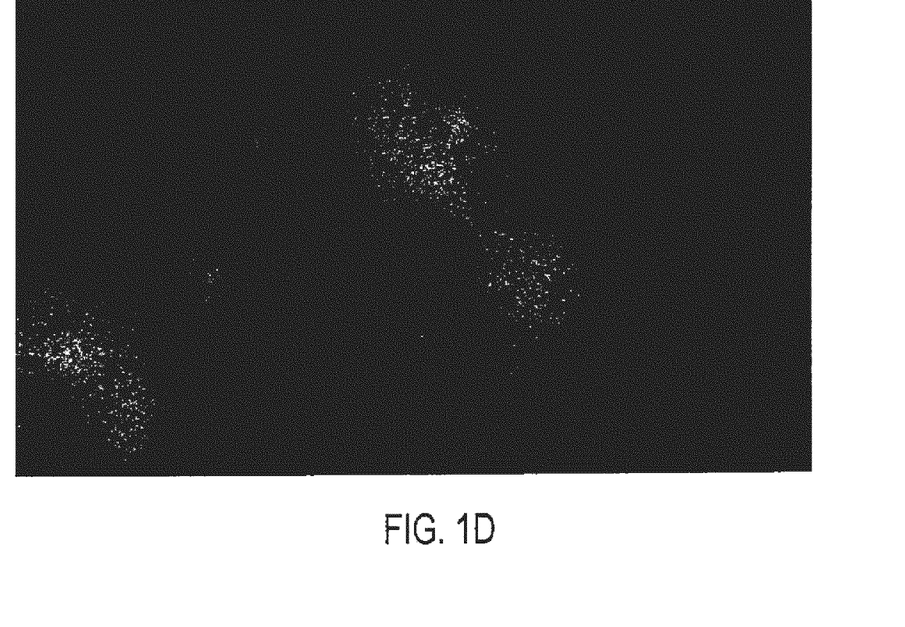
FIG. 1D is a relaxation image of a COS7 cell in which red fluorescent protein is expressed.

FIG. 1D shows a relaxation image of COS7 cell in which red fluorescent protein (RFP) is expressed. The COS7 cell was imaged in three phases: (1) with no magnet present; (2) with a 0.5 Tesla magnetic field applied parallel to the electromagnetic field propagation vector used to excite the sample for anywhere from 1-3 seconds to 80-90 seconds; and (3) after the magnet was withdrawn. The image in FIG. 1D is a result of analysis of the third phase (in contrast, in the first phase there is photo-bleaching due to continuous excitation, but no magnetic relaxation). It was acquired by capturing video imagery (e.g., AVI video data) of the live COS7 cell expressing RFP was recorded. A processor extracted individual frames (including the one shown in FIG. 1D) from the live images and determined the fluorescence intensity per unit area.

Fluorescence Enhancement with Static Magnetic Fields

Figure 2:
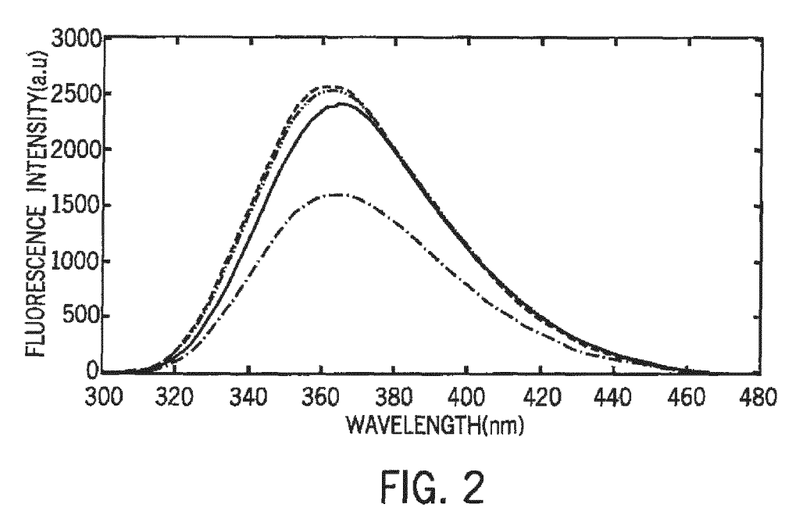
FIG. 2 is a plot that shows tryptophan's fluorescence emission spectrum at magnetic field strengths of 0.0 Tesla (dashed and dotted line), 0.035 Tesla (asterisks), 0.05 Tesla (dots), and 0.07 Tesla (crosses).

A static magnetic field (e.g., with a strength of about 0.05-0.07 Tesla) enhances the fluorescence intensity of quantum dots, tryptophan, pi-ring-based systems, and other compounds. For instance, a magnetic field may enhance the fluorescence emission of pi-ring-based aromatic amino acids (illustrated in FIG. 2), tyrosine, pyrene, and propidium iodide. Increasing the magnetic field strength increases the enhancement effect up to a saturation level; in FIG. 2, this saturation is occurs at about 0.035 Tesla. FIG. 2 also shows that a static magnetic field may also cause a blue shift of light emitted by pi-ring-based systems, which may which may be accounted for by the pi-pi assembly in these systems.

Figure 3A:
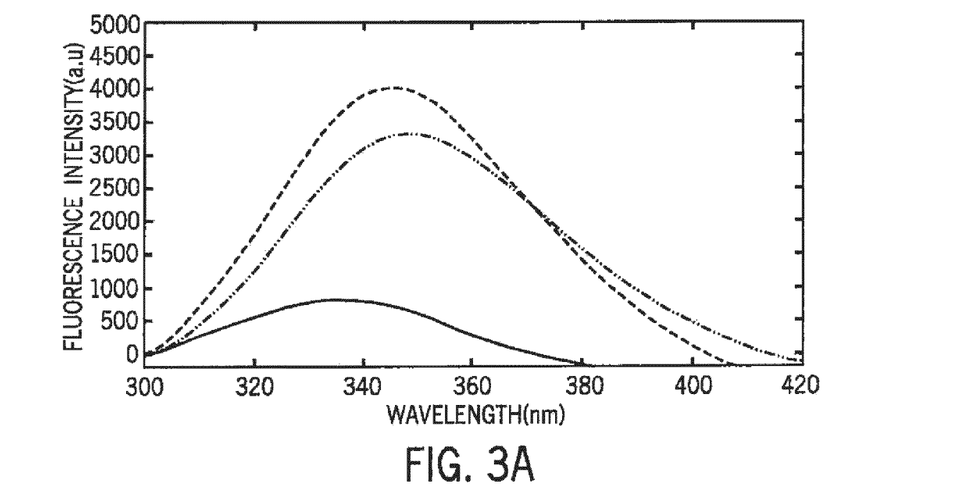
FIGS. 3A-3C are plots of fluorescence emission spectra at magnetic field strengths of 0.0 Tesla (crosses) and 0.07 Tesla (diamonds) and difference emission spectra (squares) for bovine serum albumin (BSA) (FIG. 3A), aldolase (FIG. 3B), and fibrinogen (FIG. 3C).
Figure 3B:
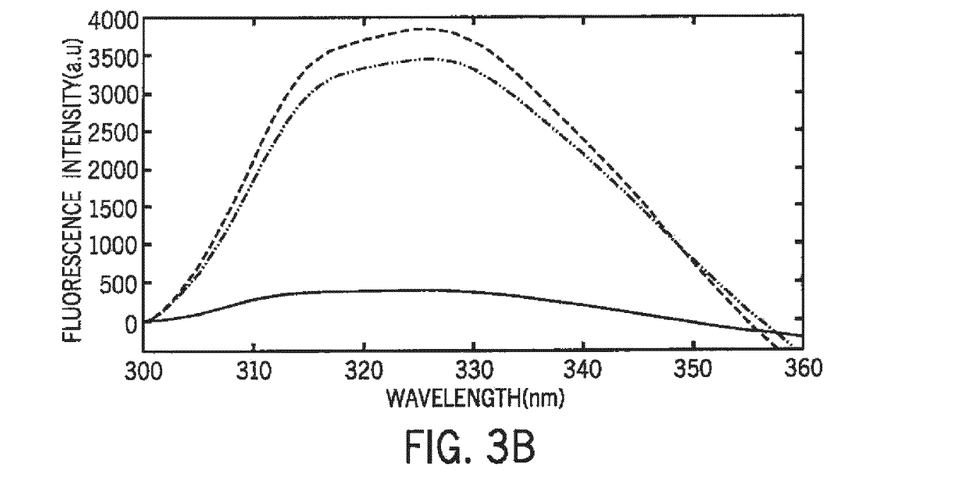
Figure 3C:
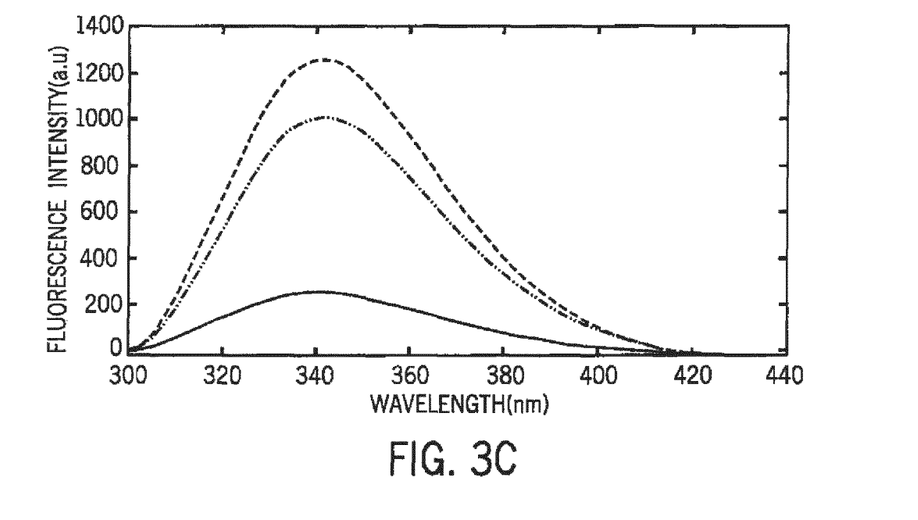

FIGS. 3A-3C illustrate the effect of a static magnetic field on the intrinsic fluorescence of 3 mL cuvettes containing three different proteins at identical molar concentrations: bovine serum albumin (BSA) (FIG. 3A), aldolase (FIG. 3B), and fibrinogen (FIG. 3C). More specifically, the upper line in each plot represents the fluorescence emission spectrum when the sample is in the presence of a 0.07 Tesla magnetic field. The middle line in each plot represents the fluorescence emission spectrum when the sample is not subject to a magnetic field. And the lower line in each plot represents the middle line from the upper line—the difference in emission spectra, or difference emission spectrum.

Figure 4:
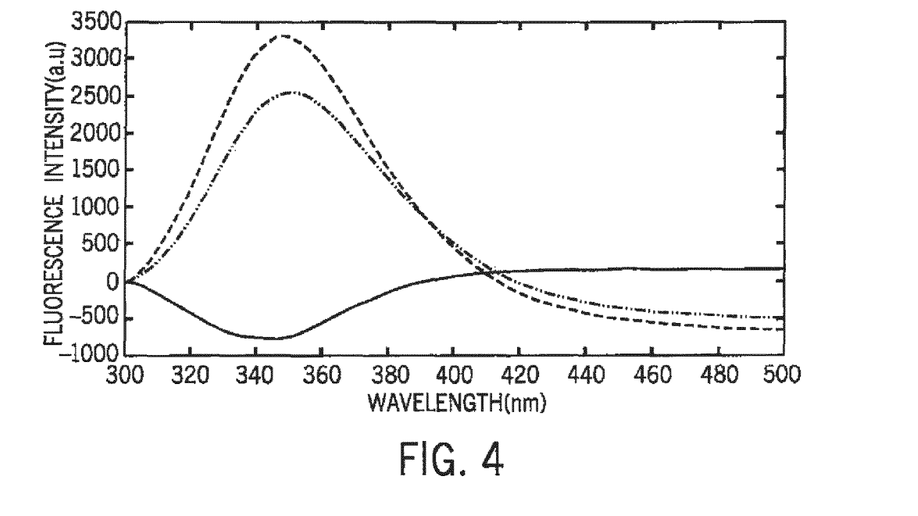
FIG. 4 is a plot of the fluorescence spectrum in the presence of a magnetic field (upper curve), the fluorescence spectrum in the absence of a magnetic field (middle curve), and the difference emission spectrum (lower curve) that illustrates the volume effect in a protein.

FIGS. 3A-3C show that each sample responds to the static magnetic field by showing a characteristic enhancement pattern. Maximal enhancement occurs in fibrinogen, which contains the maximal number of the tryptophan residues. (FIG. 4 shows that a reversal of the difference spectrum for fibrinogen may occur with a 1 mL fluorescence cuvette instead of a 3 mL cuvette as in FIG. 3C). Without being bound by any particular theory, the difference in enhancement appears to originate in the difference in number, distribution, and local environment of tryptophan and tyrosine rather than in the molar concentration because each sample has the same molar concentration. Because the signatures are different for identical molar concentrations, these enhancement patterns can be used as fingerprints to identify or classify known or unknown samples. In addition, the volume of the container (fluorescence cuvette) may have a role in the magnetic field induced enhancement of fluorescence emission.

Relaxation Behavior and Optical Memory Effects

A sample may also be identified from its magnetically induced relaxation and optical memory behaviour. The systems can retain the magnetic exposure even after the withdrawal with a relaxation time $T_F$ that is on the order of seconds. Proteins (e.g., fibrinogen) may relax more slowly than small fluorophores (e.g., tryptophan). This is reflected by the relative $T_F$ values of the two, where $T_F$ is obtained by the following relaxation equation:

$$\frac{dF}{dt} = \frac{(F_0 - F)}{T_F} - C \qquad (1)$$

where F is the fluorescence intensity, $F_0$ is the fluorescence intensity in the absence of any magnetic field, and C is a constant that depends on the nature and local environment of the fluorophores. It may also depend on the bleaching profile, which may follow first-order kinetics.

Figure 5A:
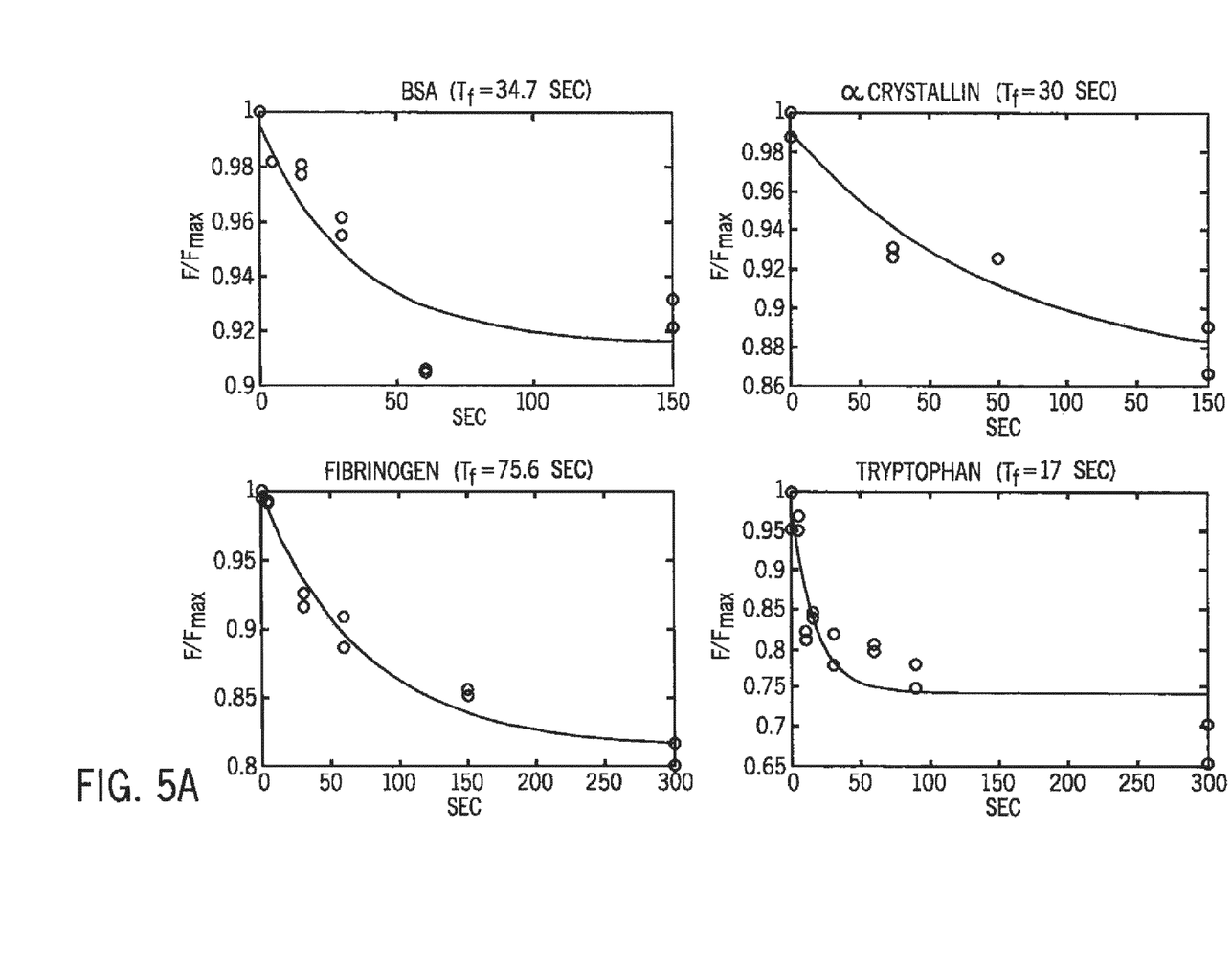
FIG. 5A includes plots of fluorescence relaxation profiles for bovine serum albumin (upper left), α-crystallin (upper right), fibrinogen (lower left), and tryptophan (lower right) after exposure to a magnetic field.
Figure 5B:
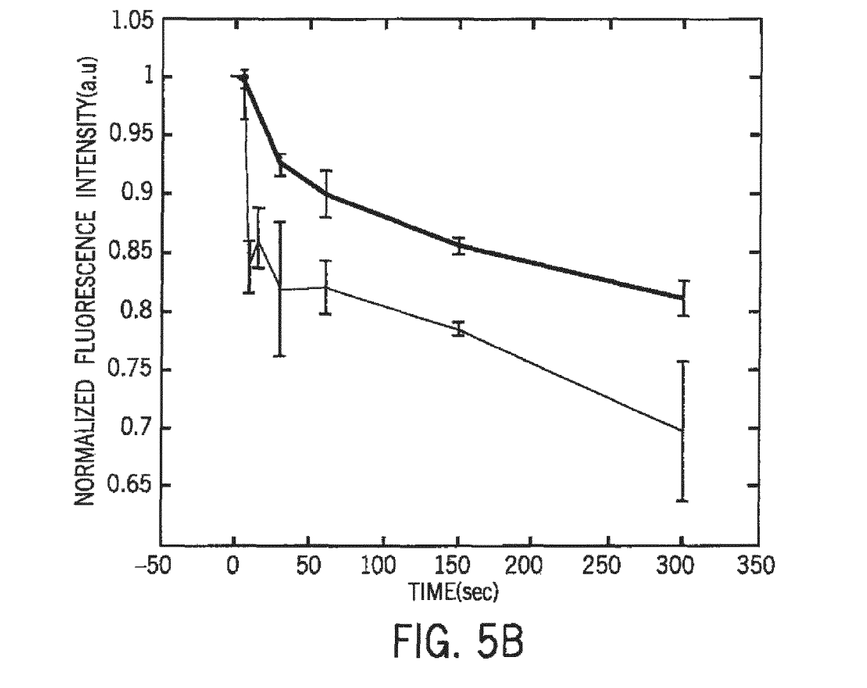
FIG. 5B shows a plot of the relaxation profile of tryptophan (gray line) and fibrinogen (black line).

FIG. 5A is a plot of relaxation times for BSA (upper left), α-crystallin (upper right), fibrinogen (lower left), and tryptophan (lower right). Each plot shows measured intensity values (circles) versus time and a corresponding fit (lines) versus time derived using Equation (1). FIG. 5B shows that the estimated relaxation time of tryptophan is about 16 seconds, whereas that of fibrinogen is about 76 seconds. Without wishing to be bound by any particular theory, it appears that this difference in $T_F$ may be due to tryptophan's different environment. In a protein, tryptophan may have a more rigid environment with fewer degrees of freedom. This difference may cause differences in the magnetic enhancement of fluorescence and relaxation that can be used to identify bio-molecules (e.g., proteins).

A magnetic field also affects the dipolar excitations responsible for the 280 nm absorbance. A roughly 28% enhancement is observed in this absorbance (from 0.1215±0.0106 to 0.156±0.0042). Perturbations in the sample's alignment with respect to the excitation electric vector caused by the magnetic field may affect the sample's anisotropy. For instance, the anisotropy value of pure tryptophan (0.008) may be reduced to (−0.0085). For fibrinogen, the anisotropy reduction is less significant (changes from 0.0742±0.0051 to 0.0719±0.0083). Without being bound by any particular theory, these absorbance and anisotropy measurements suggest that for bio-molecules a component of the magnetic field effect is due to spin orientation. This effect appears to be smaller in more rigidly connected fluorophores.

Apart from alignment, an alternative mechanism of fluorescence enhancement may be the formation of quantum coherent state through coupling of nuclear and electronic spin states. It has been suggested that migratory birds use this type of quantum phenomenon to detect the geomagnetic field for navigation purposes. The de-coherence time of such a quantum coherent state is about 100 μs, which is much larger than that of artificial systems like condensed or superconducting systems. However, an alternative de-coherence mechanism at a higher field (e.g., 0.07 T) may explain the occurrence of high $T_F$ value. The alternative mechanism may involve triplet-state fusion as well as a spin lattice relaxation.

Figure 6A:
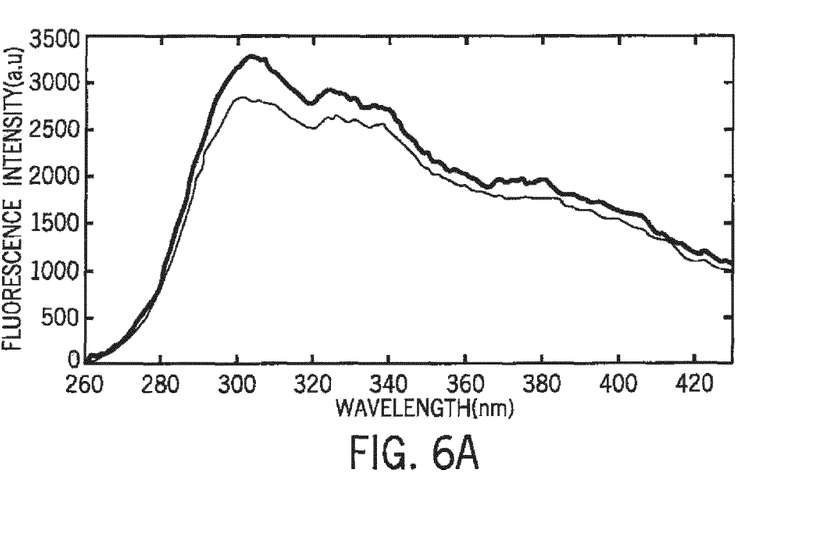
FIG. 6A is a plot of the fluorescence emission spectrum for a silicon quantum dot in the presence (asterisks) and absence (crosses) of a 0.07 Tesla magnetic field.
Figure 6B:
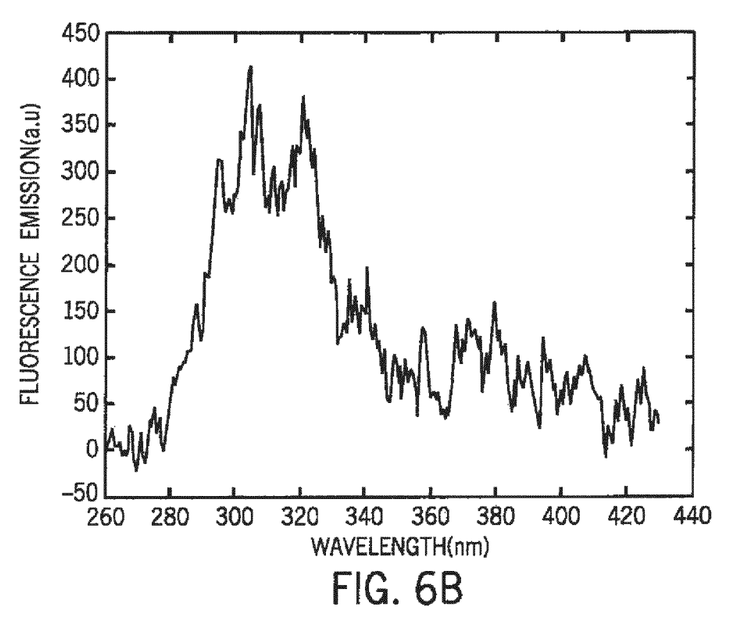
FIG. 6B is a plot of the difference emission spectrum for the silicon quantum dot of FIG. 6A.
Figure 6C:
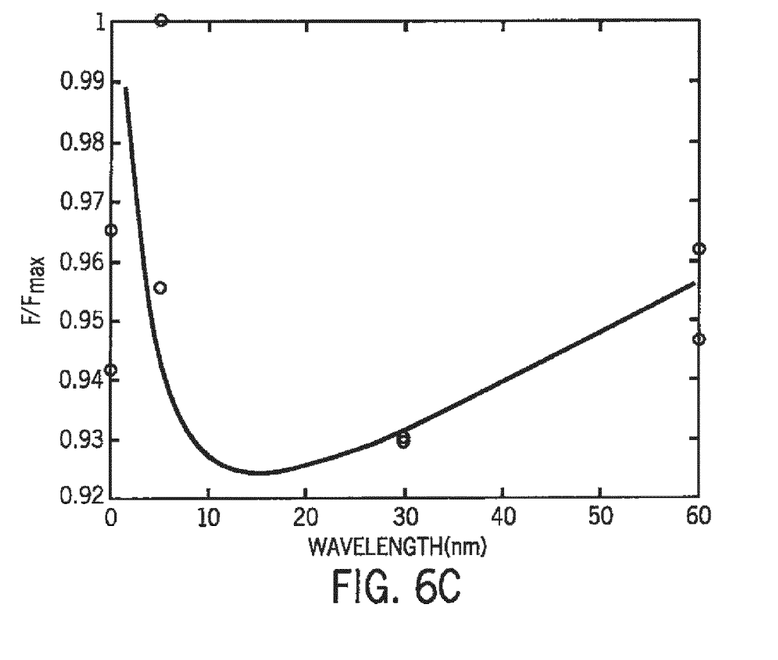
FIG. 6C is a plot that illustrates the relaxation behavior of the silicon quantum dot of FIGS. 6A and 6B.

FIGS. 6A and 6B illustrate how the fluorescence enhancement and relaxation behavior induced by a static magnetic field can be used as an alternative protein finger printing technique. FIG. 6A shows the fluorescence emission spectrum of a silicon dot in the presence of a 0.07 Tesla magnetic field (upper curve) and without any magnetic field present (lower curve). FIG. 6B shows the difference between the upper and lower curves in FIG. 6A. FIG. 6C shows measurements (circles) and a fit (solid line) of the relaxation of the silicon quantum dot's fluorescence emission up removal of the magnetic field. FIGS. 6A and 6B show that the magnetic field causes the quantum dot's emission spectrum to increase in intensity and to shift. Because the silicon quantum dot's difference spectrum and the relaxation curve behave differently from those of proteins, it is possible to discriminate between quantum dots and other materials using these measurements. Other nanostructures (not showing fluorescence) embedded with quantum dots can also be classified in similar way.

Auto-Fluorescence and Fluorescence Imaging

Auto-fluorescence (e.g., in bio-systems) is generally considered to be an undesirable attribute of fluorescence imaging. Auto-fluorescence emerges from a number of naturally occurring cellular metabolites. The following table shows auto-fluorescence excitation and emission wavelengths for fluorophores of different biological origin:

| Biological Origin | Fluorophores | Excitation Wavelength (nm) | Emission Wavelength (nm) |
|---|---|---|---|
| Bacteria | NAD(P)H | 260 | 450 |
| Plants | Chlorophyll | 460 | 660 |
|  | Polyphenols | 280 | 530 |
| Animals, Eukaryotes, and Prokaryotes | NAD(P)H | 260 | 450 |
|  | Tyrosine | 270 | 405 |
|  | Tryptophan | 290 | 330 |
|  | Riboflavin | 450 | 556 |
| Animal | AGE products (diabetes) | 350 | 450 |
|  |  | 400 | 560 |
|  | Melanin |  | Higher auto-fluorescence at different wavelengths |
|  | Cancer Cells |  |  |

Changes in a sample's auto-fluorescence emission caused by a magnetic field can also be used to identify, classify, or discriminate the sample. To understand why, consider a given cell to be a combination of a few auto-fluorescing fluorophores that emit light at one or more emission wavelengths ($\lambda_{em}$) upon irradiation at a given combination of excitation wavelengths ($\lambda_{ex}$). Let $AF_i$ be the contribution to the total auto-fluorescence from the $i^{th}$ fluorophore. Summing the contributions of the individual fluorophores gives an overall auto-fluorescence of:

$$AF = \sum_i AF_i. \qquad (2)$$

When subjected to a magnetic field, the $i^{th}$ fluorophore's autofluorescence changes from $|AF_i|$ to $|AF_{im}|$ with $|AF_{im}| > |AF_i|$. The relaxation response of the entire set of fluorophores to a magnetic field can be expressed by the general sets of equations:

$$\frac{d\Delta AF_{1m}}{dt} = F_i(\Delta AF_{1m}, \Delta AF_{2m}, \ldots). \qquad (3)$$

Where $F_i$ represents an algebraic sum of contributions from individual fluorophores and is a function of $AF_{im}$. Equation (3) can be linearized around a steady state and expressed as:

$$\frac{d\Delta AF_{im}}{dt} = R\Delta AF_{im} \qquad (4)$$

where $\Delta AF_{im}$ is a column vector representing the different auto-fluorescence components.

The dynamics of the relaxation process are dictated by the eigenvalues of the R matrix. The observation can be guided by the smallest eigenvalues, which may be dimensionally equivalent to the largest relaxation time(s). The eigenvalues reflect the inverse of the relaxation times of the component fluorophores participating in the auto-fluorescence. The eigenvalue with the lowest magnitude represents the slowest relaxation process, and the eigenvalue with the highest magnitude represents the fastest relaxation process. Let the lowest relaxation (i.e., smallest λ) is given by $T_{af}$.

The system of equations (2)-4) is derived for a given cell type. In other words, $T_{af}$ is a function of local cellular environment, which means that the auto-fluorescence relaxation may provide a fingerprint of the cell type (e.g., its state of differentiation). For instance, imaging an auto-fluorescent cell or sample during relaxation may make it possible to identify different regions within the sample based on their respective relaxation times. Because the magnetic relaxation depends on spin memory at every point location in the cell or sample, the relaxation time can be expressed as a function of the one or more spatial dimensions (e.g., x, y, and z). In other words, one can generate an (x, y) map of the auto-fluorescence at a given plane in the sample.

The relaxation image of the auto-fluorescence (which can be generated by a computer from image stacks, collected at successive time intervals) provides a robust finger print of the cell. The discriminatory power of such image is particularly advantageous as it may be specific to a particular cell, a particular disease, particular growth conditions, etc. For cancer cells, such results may be valuable as the time value does not depend on the actual fluorescence (which may have detector a dependence), but depends on the internal states of the cell. Applications of cell type discrimination based on magnetically induced changes in auto-fluorescence include, but are not limited to: (1) detecting cancer cells; (2) detecting contaminants and their sources; and (3) designing probes for diseases, etc. For probe designs, comparing $T_{af}$ to the relaxation time of the probe, $T_{probe}$, makes it possible to determine the relative contribution of the auto-fluorescence. For example, it may be possible to obtain a probe image alone at longer time intervals if $T_{af} < T_{probe}$.

Magnetic Fluorescence Relaxation in Graphene-Based Systems

The fluorescence imaging based approach described above can be used to characterize graphene-based samples by exploiting: (1) the super fluorescence quenching capacity of graphene and graphene oxide; and (2) the unique fluorescence of grapheme-based systems. In some cases, the structure of graphene-based sample can be deduced or determined from an image or map that shows (a) how the fluorescence quenching varies with time; (b) how the auto-fluorescence, if any, varies with time; and (c) how this dependence varies at different spatial points.

At each point (x,y) the quenching efficiency may depend on the accessibility of the fluorophores to the quencher (e.g., graphene oxide). If there exists a square matrix z whose dimension is of the order of the size of x or y, then one can map the (x, y) points on the matrix z, with the null elements of the matrix representing the rows (Y values) or columns (X values) for which there is or was no quenching (possibly because the fluorophore is not accessible). Once mapped, the z matrix represents an image of the quenching profile of the imaged object. The quenching surface may change depending on (i) the application of a magnetic field and/or (ii) the change of the magnetic field. As a result, the elements of the image matrix Z become magnetic field dependent. The differentials of Z represent how the quenching surface changes in response to both exposure to a field and withdrawal of the field. This differential image in turn can provide structural information about the imaged object.

Consider graphene doped with fluorescent silicon or iron quantum dots. Such material may exhibit a magnetic memory behavior, which involves characteristic temporal dynamics fluorescence during magnetic relaxation. In the case of a quantum dot sample doped with graphene, this magnetic memory can be observed by: (i) inducing graphene's super-quenching effect on a background fluorophore in the sample; (ii) imaging the sample in the presence of a static magnetic field (e.g., of about 0.05 Tesla to about 0.1 Tesla); (iii) imaging the sample in the absence of any magnetic field; (iv) taking the difference of the images; and classifying or identifying the graphene or its structure based on the difference of the images. If desired, the imaging in steps (ii) and (iii) may include taking single snapshots or acquiring successive frames of image data (e.g., video data). This classification process may be particularly useful for identifying, classifying, or studying graphenes conjugated with peptides. Peptide and protease fingerprinting is also possible using these techniques.

EXAMPLES

Example 1

Fluorescence Correlation Spectroscopy

As understood in the art, fluorescence correlation spectroscopy (FCS) involves measuring a sample's fluorescence spectrum (e.g., using a confocal microscope or a two-photon excitation microscope) and performing an auto-correlation of the measured fluorescence spectrum. FCS can be used to determine the concentration, size, and diffusion path(s) of fluorescent particles (e.g., molecules) in very small spaces. In one example, a researcher exposes a sample with a picomolar to nanomolar concentration of fluorescent particles to a 0.07 Tesla magnetic field for about five minutes. The researcher removes the magnetic field, excites the sample with a laser beam, and images the sample with a confocal microscope until the fluorescence decays. A CCD optically coupled to the microscope records successive images of the sample as the fluorescence decays and stores the images in a memory. The researcher may also excite the sample a second time (in the absence of the magnetic field) and acquire a second series of images of the sample as the fluorescence decays again.

A processor coupled to the memory computes the auto-correlation for each pixel in the image. Based on the auto-correlation data, the processor estimates the concentration of the fluorescent particles at each location in the image. The processor may also compute the fluorescence relaxation time associated with the fluorophore at each pixel location and determine the fluorophore type based on relaxation time. In addition, it may compare the fluorescence correlation spectra acquired after the sample was exposed to the magnetic field to the fluorescence correlation spectra acquired with no exposure to the magnetic field.

Example 2

Flow Cytometry

As understood in the art, flow cytometry is a technique for counting and examining microscopic particles, such as cells and chromosomes, by suspending them in a fluid stream and passing the fluid stream through a detection apparatus. In this case, the fluid passes through a laser beam that excites fluorophores in the fluid. A detector senses light emitted by the excited fluorophores. The fluid then passes through a magnetic field (e.g., of about 0.035 Tesla to about 0.00.10 Tesla) for 30 seconds to about 5 minutes before passing through the laser beam a second time. Another detector senses the light emitted by the fluorophores, and a processor coupled the detectors determines the difference, if any, between the signals from the detectors and uses the result to identify or classify the fluorophore. Based on this identification, the processor applies a positive or negative charge to fluorophore. Charged electromagnets pull or push the charged particle into a vessel or path based on the fluorophore's charge as understood in the art.

Example 3

Cancer Cell Detection

A physician uses a magnetically induced fluorescence endoscope to generate discriminate cancer cells from other cells. First, the physician inserts the endoscope, e.g., into the patient's esophagus (e.g., for diagnosing Barrett's esophagus) or into one of the patient's blood vessels as known in the art. Next, the physician maneuvers the endoscope into a position suitable for imaging the tissue of interest. The physician exposes the tissue to a magnetic field, either by placing the patient in a magnetic field or by actuating an electromagnet disposed at the end of the endoscope. After a brief exposure period (e.g., 60 seconds), the physician removes the magnetic field (e.g., by removing the patient from the magnetic field or by turning off the electromagnet) and irradiates the tissue with light from a laser or another suitable light source. The physician uses the endoscope to collect video images of tissue, which fluoresces in response to the irradiation. A memory coupled to the endoscope records the image data, and a processor coupled to the memory processes the image data as described above and compares the processed images to a library or database of different cell types. The processor then indicates, via a display or other interface, that the tissue matches or does not match the reference data stored in the database. In some cases, the processor may also indicate the confidence of the match.

The subject matter described herein sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or to wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone. B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A method of discriminating a fluorescent region of a sample, the method comprising:
   determining a first relaxation time associated with a decay of the fluorescence of at least part of the fluorescent region in the absence of a magnetic field;
   determining a second relaxation time associated with a decay of the fluorescence of the at least part of the fluorescent region in the presence of the magnetic field;
   performing a comparison of the first relaxation time to the second relaxation time to determine a difference between the first relaxation time and the second relaxation time; and
   identifying the at least part of the fluorescent region based on the comparison of the first relaxation time to the second relaxation time and the difference between the first relaxation time and the second relaxation time.

2. The method of claim 1, wherein the sample comprises at least one of a biological sample, a tissue, a cell, a particle, a protein, and a particle tagged with a fluorophore.

3. The method of claim 1, further comprising setting a strength of the magnetic field to be about 35 mT to about 100 mT.

4. The method of claim 1, wherein determining the first relaxation time comprises obtaining a first series of images of the at least part of the fluorescent region, and wherein determining the second relaxation time comprises obtaining a second series of images of the at least part of the fluorescent region.

5. The method of claim 4, further comprising:
   determining a change in a first fluorescence spectrum associated with the at least part of the fluorescent region from the first series of images;
   determining a change in a second fluorescence spectrum associated with the at least part of the fluorescent region from the second series of images; and
   wherein performing the comparison of the first relaxation time to the second relaxation time comprises comparing the change in the first fluorescence spectrum to the change in the second fluorescence spectrum.

6. The method of claim 1, wherein the first relaxation time corresponds to a relaxation associated with at least one process that is not affected by the magnetic field.

7. The method of claim 1, further comprising:
   discriminating between the at least part of the fluorescent region and another part of the fluorescent region based on the comparison of the first relaxation time to the second relaxation time.

8. The method of claim 1, further comprising:
   determining a change in an emission wavelength of the fluorescent region in the presence of the magnetic field.

9. The method of claim 1, further comprising:
   applying the magnetic field to the sample; and
   withdrawing the magnetic field to create the absence of the magnetic field.

10. The method of claim 1, wherein identifying the at least part of the fluorescent region comprises identifying at least one of a quantum dot, an organic molecule, an aromatic amino acid, a protein, or another fluorescent material.

11. The method of claim 1, further comprising applying the magnetic field to the fluorescent region, wherein applying the magnetic field comprises orienting a magnetic field vector associated with the magnetic field perpendicular to an electric field vector associated with an electromagnetic field used to induce fluorescence of the fluorescent region.

12. The method of claim 11, wherein applying the magnetic field comprises varying an orientation of a magnetic field vector associated with the magnetic field.

13. The method of claim 12, further comprising:
   measuring a change in the fluorescence as a function of the orientation of the magnetic field vector; and
   identifying the at least part of the fluorescent region based on the change in the fluorescence.

14. The method of claim 1, wherein at least part of the fluorescent region exhibits autofluorescence.

15. A system comprising:
   a magnet configured to provide a magnetic field;
   a switch configured to control application of the magnetic field to a fluorescent region of a sample;
   a camera configured to image at least part of the fluorescent region in the presence of the magnetic field; and
   a processor operably coupled to the camera and configured to:
      determine a first relaxation time associated with a decay of the fluorescence of the at least part of the fluorescent region in an absence of the magnetic field,
      determine a second relaxation time associated with a decay of the fluorescence of the at least part of the fluorescent region in the presence of the magnetic field,
      perform a comparison of the first relaxation time to the second relaxation time to determine a difference between the first relaxation time and the second relaxation time, and
      identify the at least part of the fluorescent region based on the difference between the first relaxation time and the second relaxation time.

16. The system of claim 15 wherein the magnet is further configured to provide the magnetic field at a strength of about 35 mT to about 100 mT.

17. The system of claim 15 wherein the switch is further configured to vary an orientation of the magnetic field with respect to the fluorescent region.

18. The system of claim 15, wherein, to determine the first relaxation time, the processor is configured to obtain a first series of images of the at least part of the fluorescent region, and wherein, to determine the second relaxation time, the processor is configured to obtain a second series of images of the at least part of the fluorescent region.

19. The system of claim 18, wherein the processor is further configured to:
   determine a change in a first fluorescence spectrum associated with the at least part of the fluorescent region from the first series of images;
   determine a change in a second fluorescence spectrum associated with the at least part of the fluorescent region from the second series of images; and
   wherein to perform the comparison of the first relaxation time to the second relaxation time, the processor is configured to compare the change in the first fluorescence spectrum to the change in the second fluorescence spectrum.

* * * * *

UNITED STATES PATENT AND TRADEMARK OFFICE
CERTIFICATE OF CORRECTION

PATENT NO. : 9,459,210 B2  
APPLICATION NO. : 13/884721  
DATED : October 4, 2016  
INVENTOR(S) : Dasgupta et al.

Page 1 of 1

It is certified that error appears in the above-identified patent and that said Letters Patent is hereby corrected as shown below:

In the Specification

Column 1, Line 9, delete "§371" and insert -- § 371 --, therefor.

Column 4, Line 44, delete "laser, an" and insert -- laser; an --, therefor.

Column 5, Line 5, delete "photocurrent. whose" and insert -- photocurrent, whose --, therefor.

Column 6, Line 25, delete "saturation is occurs" and insert -- saturation occurs --, therefor.

Column 8, Line 37, delete "$AF_t$," and insert -- $AF_i$ --, therefor.

Column 9, Line 11, delete "(2)-4)" and insert -- (2)-(4) --, therefor.

Column 9, Line 32, delete "detector a dependence)," and insert -- detector dependence), --, therefor.

Column 12, Line 1, delete "and/or to wirelessly" and insert -- and/or wirelessly --, therefor.

Column 12, Line 46, delete "A alone. B" and insert -- A alone, B --, therefor.

Signed and Sealed this  
Twenty-first Day of February, 2017

Michelle K. Lee  
*Director of the United States Patent and Trademark Office*